United States Patent [19]

Devaney, Jr.

[11] Patent Number: 5,098,660
[45] Date of Patent: Mar. 24, 1992

[54] TRANSFER APPARATUS FOR CHEMICAL REACTION PACK

[75] Inventor: Mark J. Devaney, Jr., Rochester, N.Y.

[73] Assignee: Eastman Kodak Company, Rochester, N.Y.

[21] Appl. No.: 461,944

[22] Filed: Jan. 8, 1990

[51] Int. Cl.$^5$ .................. B30B 5/02; B30B 15/34; B01L 11/00; G05D 23/00
[52] U.S. Cl. ................................. 422/99; 422/109; 100/93 P; 100/211; 100/266
[58] Field of Search .............. 422/58, 63, 68.1, 102, 422/104, 61, 99, 109; 100/93 P, 211, 266

[56] References Cited

U.S. PATENT DOCUMENTS

| | | | |
|---|---|---|---|
| 2,406,403 | 8/1946 | Rogers | 100/266 |
| 3,476,515 | 11/1969 | Johnson et al. | 422/61 |
| 3,998,580 | 12/1976 | Pfeiffer | 100/93 P |
| 4,046,500 | 9/1977 | Pfeiffer | 100/93 P |
| 4,193,341 | 3/1980 | Clements et al. | 100/211 |
| 4,228,926 | 10/1980 | Gordon | 222/103 |
| 4,350,585 | 9/1982 | Johansson et al. | 210/96.1 |
| 4,390,499 | 6/1983 | Curtis et al. | 422/63 |
| 4,673,657 | 6/1987 | Christian | 436/501 |

*Primary Examiner*—Robert J. Warden
*Assistant Examiner*—Theresa A. Trembley
*Attorney, Agent, or Firm*—Dressler, Goldsmith, Shore, Sutker & Milnamow, Ltd.

[57] ABSTRACT

An apparatus for transferring a test liquid between chambers of a chemical reaction pack. The apparatus includes a series of actuation modules arranged in adjacent relationship to each other to define chemical reaction pack receiving stations therebetween. Each actuation module includes pressure applicators for applying external pressure to the chambers of the reaction pack and temperature control elements for heating and cooling the test liquid within the chemical reaction pack.

20 Claims, 2 Drawing Sheets

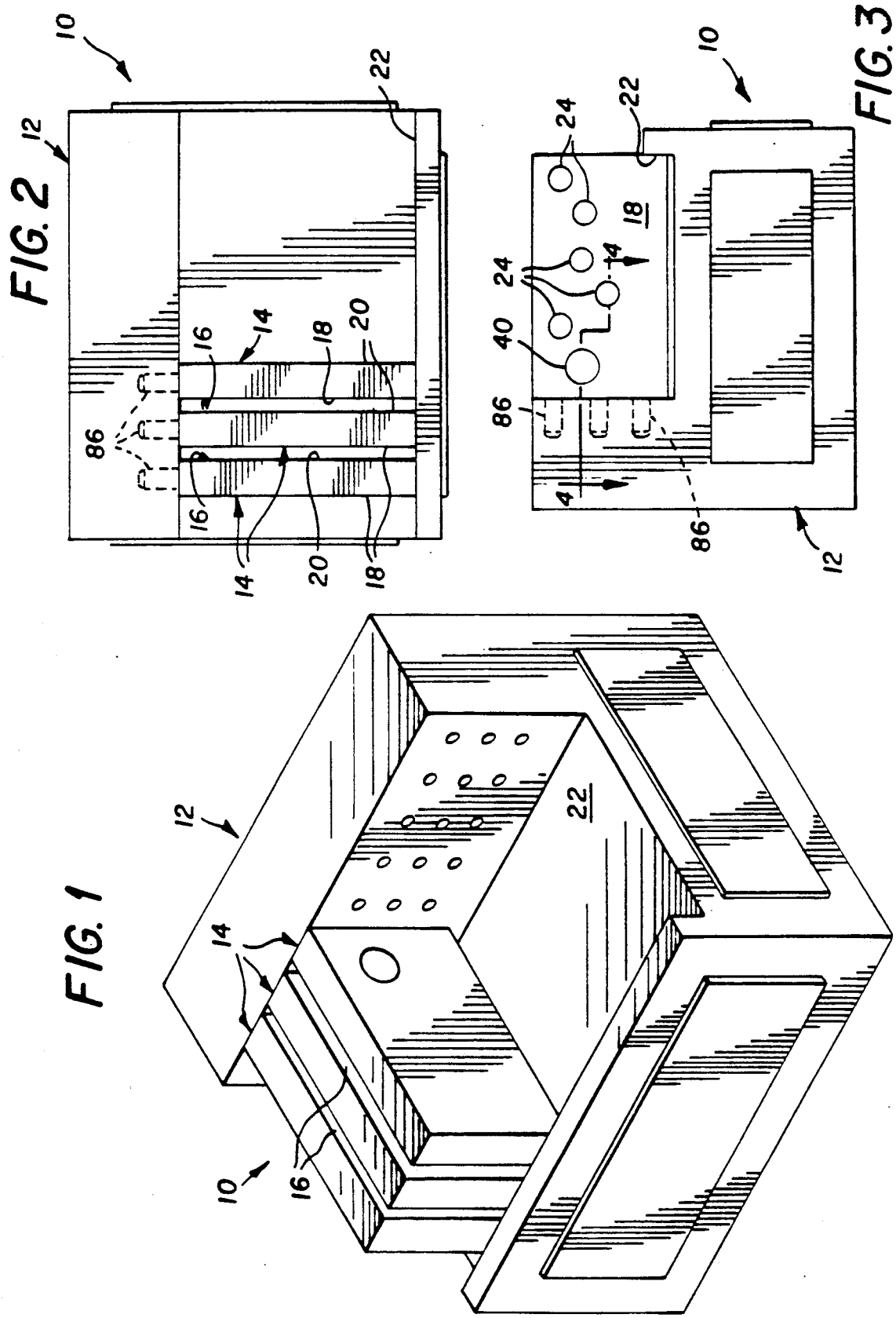

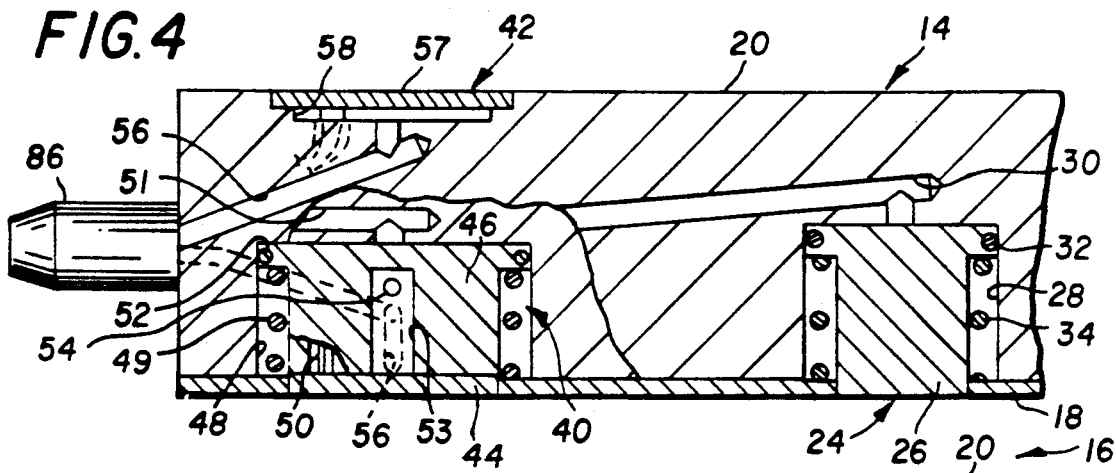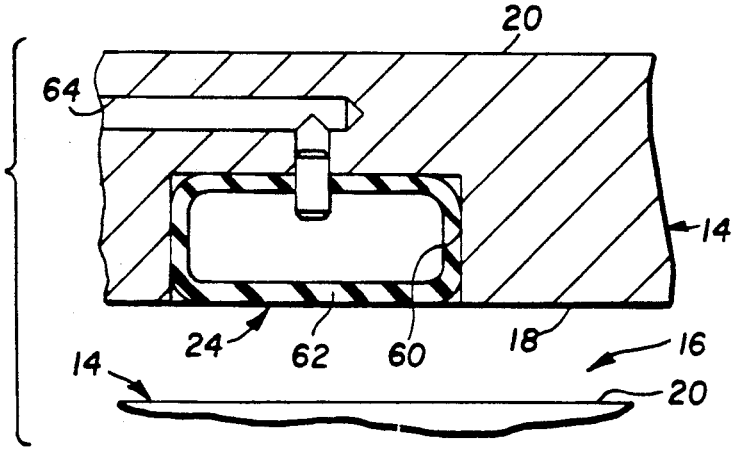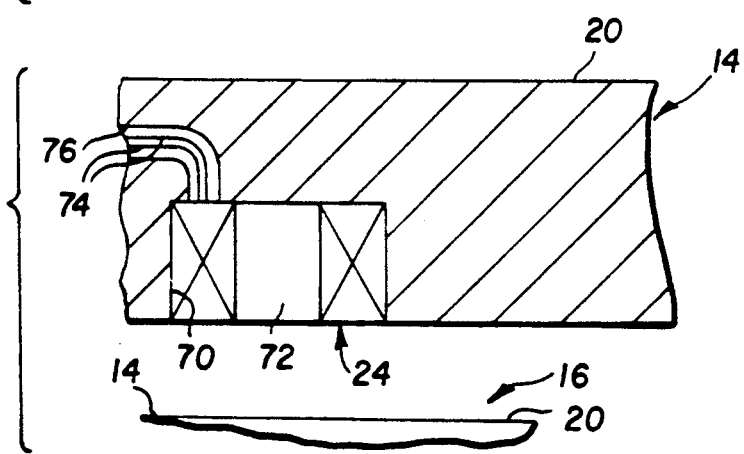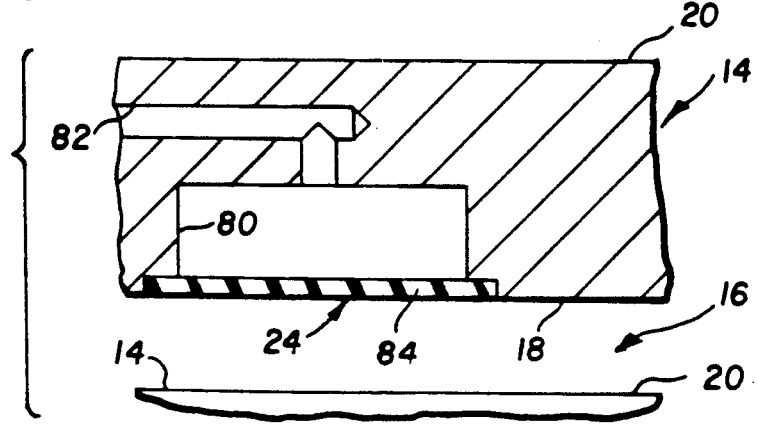

TRANSFER APPARATUS FOR CHEMICAL REACTION PACK

FIELD OF THE INVENTION

The present invention relates to an apparatus for transferring a test fluid between adjacent chambers of a chemical reaction pack.

BACKGROUND OF THE INVENTION

Disposable chemical reaction packs for use in automatic analysis equipment are known in the art. Such reaction packs typically comprise a pliable body fabricated from a fluid impermeable material. The body of the reaction pack is divided into successive individual compartments or chambers that each have a blister-like configuration and are normally separated from each other with seals which are rupturable or openable in response to sufficient pressure being applied to such seals. One or more of the compartments or chambers contain predetermined amounts of reagents with which a test liquid reacts.

By applying increasing external pressure to the blister-like chambers, the normally closed seals are opened to permit transfer of the contents of one chamber to an adjacent chamber. The transfer of the test liquid between chambers and the intermixing thereof with reagents is preferably accomplished without opening the reaction pack.

Manually applying external pressure to each blister-like chamber of the reaction pack to establish sufficient internal pressure to open a normally closed seals is tedious, time consuming, inexact, and could result in damage to the reaction pack. Inconsistency or variations in pressure and time can adversely affect chemical reactions within the pack and lead to inaccurate results. It would be beneficial, therefore, to automate the process of transferring liquids through a reaction pack without requiring the reaction pack to be opened.

The liquids in the reaction pack may be subjected to temperature changes during the test procedure. It has been found, for example, that thermal cycling by heating and cooling a metal block on which a reaction pack is situated is relatively slow and inefficient. Accordingly, there is a need and desire for a device which automatically transfers liquids between chambers in a reaction pack while heating and/or cooling the liquids.

SUMMARY OF THE INVENTION

In accordance with the present invention, there is provided a processing apparatus for transferring a liquid between chambers of a chemical reaction pack without requiring the reaction pack to be opened. The apparatus of the present invention further includes temperature control elements for heating and cooling the liquid within the chemical reaction pack as the liquid is transferred therethrough.

The apparatus of the present invention includes at least two actuation modules arranged side-by-side to define a chemical reaction pack receiving station between confronting major surfaces on the actuation modules. At least one of the actuation modules includes pressure applicators for applying external pressure against at least one chamber of the reaction pack to transfer the test liquid between the chambers.

Each actuation module defines two generally planar major surfaces which extend substantially parallel to each other and generally parallel with like surfaces on an adjacent actuation module. The distance between confronting planar surfaces of the two adjacent actuation modules is preferably equal to the thickness of the chemical reaction pack.

In one form, the pressure applicators include a series of pistons. Each piston is arranged for movement along a path extending generally or orthogonal to a first major surface of the module. The piston defines a rigid element which is pressed against a chamber of the reaction pack under the influence of a pressurized fluid.

Alternatively, the pressure applicators can be in the form of a flexible membrane arranged for distention relative to a confronting major surface on an adjacent actuation module. Distention of the flexible membrane is effected under the influence of a pressurized fluid. Moreover, the pressure applicator may take the form of an air filled bladder. Preferably, the pressurized fluid for operating the pressure applicators is air.

In a preferred form, each of the actuator modules further include temperature control means for heating and cooling of the liquids within the reaction pack. The temperature control means comprises a first heater/cooler mechanism which is movably arranged in combination with a first module and a second heater/cooler mechanism which is carried by the second module in confronting relation with the first heater/cooler mechanism. The confronting relation between each pair of temperature control means allows the contents of the chemical reaction pack to be substantially uniformly heated or cooled.

The movable heater/cooler mechanism for heating and cooling the liquid within the reaction pack includes a thin flexible membrane which is secured to the end of a pressure applicator. The pressure applicator to which the thin flexible membrane is secured is preferably formed as a piston-like member.

With the present invention, a temperature controlling function for a reaction pack is provided at one receiving station while the pressure applicators press against a reaction pack at a second receiving station adjacent the first receiving station. The actuation modules are supported and arranged in combination with a base assembly. The base assembly contains the electronic controls and logic to cycle the actuation modules and monitor the functions thereof.

The apparatus of the present invention allows consistent and accurate transfer of the fluid through the reaction pack in an automated and simplified process. When temperature control means are arranged in combination with the actuation modules, the temperature of the test liquid in the reaction packs can be controlled during transfer of the test liquid between chambers. The modular concept provided by the present invention facilitates cleaning of the processing apparatus and allows for quick and easy servicing of the actuation modules. Furthermore, the processing apparatus of the present invention allows for expandability of this system since the base assembly can be sized according to the particular needs of a customer and does not require complete redesign of the system.

Numerous other features and advantages of the present invention will become apparent from the following detailed description, the accompanying drawings, and the appended claims.

BRIEF DESCRIPTION OF THE DRAWINGS

FIG. 1 is a perspective view of a processing apparatus embodying principles of the present invention;

FIG. 2 is a top plan view of the present invention;

FIG. 3 is a side elevational view of the present invention;

FIG. 4 is a sectional view taken along 4—4 FIG. 3 and schematically illustrating temperature control elements and pressure applicators associated with the present invention;

FIG. 5 is an alternative embodiment of a pressure applicator;

FIG. 6 is another alternative embodiment of the pressure applicator; and

FIG. 7 is still another alternative embodiment of the pressure applicator.

DETAILED DESCRIPTION OF THE INVENTION

While the present invention is susceptible of embodiment in various forms, there are shown in the drawings, and will hereinafter be described, presently preferred embodiments with the understanding that the present disclosure sets forth exemplifications of the invention which are not intended to limit the invention to the specific embodiment illustrated.

Referring now to the drawings, there is illustrated an apparatus 10 to be used in combination with one or more chemical reaction packs. More specifically, the apparatus 10 is used to facilitate transfer of a test fluid between adjacent chambers of a chemical reaction pack while maintaining the reaction pack in a sealed condition.

Each chemical reaction pack comprises a sealed hollow body formed from a fluid impermeable and pliable material which is separated or divided into a series of chambers or compartments including a storage compartment and a detection compartment. Moreover, the sealed hollow body is provided with passageways for providing fluid communication between the compartments. The hollow body is sealed along its outer periphery and preferably at all points surrounding the compartments or passageways, such as by heat and/or ultrasonic pressure sealing. A heat sensitive polymer such as ethylene vinyl acetate can be used for this purpose.

Preferably, detection materials or suitable reagents are predeposited in the chambers prior to the addition of test fluid to the reaction pack so that after the test fluid is added into the compartment, the reaction pack is sealed against leakage with no further access being required thereto. Alternatively, however, the reaction pack can be constructed to allow suitable reagents to be added to the storage compartments provided suitable means are provided to prevent the escape of contaminants into the atmosphere.

As illustrated in FIG. 1, the processing apparatus 10 of the present invention includes a base assembly 12 with a plurality of actuation modules 14 arranged in combination therewith. The actuation modules are arranged side-by-side relative to each other to define a chemical reaction pack receiving station 16 between confronting major surfaces of the modules. Preferably, the actuation modules are spaced apart a distance approximately equal to the thickness of the chemical reaction pack.

As illustrated in FIG. 2, each actuation module defines two generally planar major surfaces 18 and 20 which extend in substantially parallel relation to each other and to like surfaces on adjacent actuation modules. The base assembly 12 defines a laterally extending channel 22 wherein the actuation modules 14 are releasably accommodated.

Turning to FIG. 3, each actuation module 14 has arranged in combination therewith a plurality of pressure applicators 24 for applying external pressure against chambers or compartments of the reaction pack to facilitate transfer of the test liquid through the reaction pack. As illustrated, the pressure applicators 24 are arranged so that they are in alignment with the chambers or compartments on the reaction pack.

A preferred embodiment of a pressure applicator 24 is schematically illustrated in FIG. 4. As illustrated, each pressure applicator 24 includes a rigid piston-like element 26 accommodated within an open sided chamber 28 defined by the actuation module 14 and mounted for movement along a generally linear path extending substantially orthogonal to the major surface 18 of the actuator module.

Each actuator module further includes passageways 30 for supplying a fluid under pressure to each chamber 28 accommodating a piston-like element 26. In a preferred form, the fluid supplied under pressure to chambers 28 is preferably air. Each piston-like element 26 is appropriately sealed to retain pressure rearward thereof in the chamber 28 by means of a conventional annular seal 32. A resilient member 34 in the form of a compression spring, is arranged in combination with the piston 26 for returning it to its initial position within the actuator module.

Each actuation module further includes temperature control means for changing the temperature of the liquids within the chemical reaction packs. In a preferred form, and as illustrated in FIG. 4, the temperature control means includes a first heater/cooler mechanism 40 disposed on at least a portion of major surface 18 and a second heater/cooler mechanism 42 disposed on at least a portion of major surface 20 of each actuation module.

Although arranged on opposite major surfaces, the first and second heater/cooler mechanisms 40 and 42, respectively, are generally aligned relative to each other so that a heater/cooler mechanism on one actuation module cooperates and is aligned with a heater/cooler mechanism on an adjacent module for heating and cooling the liquid within the reaction pack disposed therebetween.

At least one of the heater/cooler mechanisms is arranged for linear displacement along a path extending generally orthogonal to a major surface of the actuation module. As illustrated, heater/cooler mechanism 40 is designed to move a heater element 44 toward and away from a reaction pack arranged between adjacent actuation modules.

In a preferred form, heater/cooler mechanism 40 includes a piston-like member 46 accommodated within an open sided chamber 48 defined by the actuation module and mounted for movement along a generally linear path. A resilient member 49, in the form of a compression spring, is arranged in combination with the piston-like member 46 for automatically returning it to its initial position within the actuator module 14.

The heater element 44 is a thin flexible membrane which is secured to the end of the piston-like member 46. In a preferred form, heater element 44 is electrically operated. Suitable electrical leads 50 passing through the piston-like member 46 provide energy to the heater element 44. The material for the heater element 44 is selected to provide a predetermined thermal path length and thermal resistance that will provide a high rate of thermal energy transfer.

The heater element can be secured to the piston-like member 46 with a layer of conventional adhesive.

Each actuation module 14 further includes passageways 51 for supplying a fluid under pressure to each chamber 48. In a preferred form, the fluid supplied under pressure to chamber 48 is preferably air. The piston-like member 46 is appropriately sealed to retain pressure rearward thereof in the chamber by means of a conventional annular seal 52.

The piston-like member 46 also defines a central passage 53 with a radial port 54 extending therefrom.

The radial port 54 is joined in fluid communication with a fluid passage 56 defined by the actuation module 14 and which provides a cooling fluid such as air to the central passage 53. After cooling, the air is vented through an aperture (not shown).

As illustrated, the stationary heater/cooler mechanism 42 is aligned with the heater/cooler mechanism 40. The stationary heater/cooler mechanism includes a heater element 57 preferably formed from a thin flexible membrane which is secured to module 14 to substantially seal a chamber 58. Heater element 57 is substantially similar to the heater element 44. Fluid passage 56 likewise directs a cooling fluid, such as air, to the chamber 58.

FIG. 5 schematically illustrates an alternative embodiment of a pressure applicator 24. As illustrated, each actuation module 14 may include a chamber 60 which opens to major surface 18 of the actuation module. An air bladder 62 is fitted within chamber 60. A passageway 64 defined by the actuation module 14 opens to the interior of bladder 62 for providing a pressurized fluid, such as air, to the the bladder 62. As will be appreciated, when pressurized fluid is introduced to its interior, the bladder 62 will expand to apply pressure upon the reaction pack between adjacent actuation modules.

Another embodiment of the pressure applicator 24 is schematically illustrated in FIG. 6. As illustrated, each module may include a chamber 70 which opens to major surface 18. A small solenoid assembly 72 is fitted within the chamber 70. Suitable electrical leads 74 extend from the solenoid assembly 72 through a passageway 76 provided or defined by module 14. Upon energization, the solenoid assembly 72 will linearly extend from the surface 18 of the actuation module in a manner applying external pressure against a chemical reaction pack.

Still another embodiment of a pressure applicator 24 is schematically illustrated in FIG. 7. As illustrated, each module may include a chamber 80 which opens to major surface 18 of the actuator module. Chamber 80 is suitably connected to a passageway 82 which delivers a fluid under pressure to the chamber. Preferably, such fluid is air. A flexible membrane 84 closes and seals the chamber 80. In a preferred form, the membrane may be glued or otherwise secured to the actuation module 14. As will be appreciated, when fluid under pressure is delivered to chamber 80, the flexible membrane 84 will expand in a manner applying external pressure to the chemical reaction pack disposed adjacent thereto.

As illustrated in FIGS. 2 and 3, each actuation module 14 includes a plurality of quick connections 86 for releasably securing the module to the base assembly 12 in a manner connecting electric power, sensors and air to each actuation module 14. The base assembly 12 contains the electronic controls and logic to cycle the actuation modules and track all the functions necessary to operate the reaction pack disposed therebetween. Included within the base assembly 12 are power and temperature controls for the temperature control means, timing controls, operator interface and a power source to operate the pressure applicator 24.

In operation, a chemical reaction pack is inserted at a receiving station 16 defined between adjacent actuation modules 14. In a preferred form, the movable heater/cooler mechanism 40 closes against a chamber of the reaction pack and pushes the reaction pack against the heater/cooler unit 42 on an adjacent actuation module. The heating/cooling units 40 and 42 then perform the required number of heating/cooling cycles.

After the heating/cooling cycle is completed, the movable heater/cooler mechanism 40 is further moved to provide sufficient external pressure against the reaction pack to break the seal so that one chamber will empty into another chamber in the proper sequence to facilitate movement of the test liquid toward a detection chamber defined on the reaction pouch. During operation, the pressure applicators 24 are timely moved to apply external pressure to additional chambers in a manner adding additional reagents to the test fluid and facilitating movement of the test liquid toward the detection chamber.

The modular concept provided by the present invention facilitates easy cleaning by the operator and more importantly allows for quick and easy servicing of the actuation modules 14. Should a chemical reaction pouch accidentally rupture, the reaction modules are easily removable for cleaning of both the actuation module 14 and the underlining base assembly 12. Furthermore, the system of the present invention provides for expansion of this system since systems of different sizes requires only redesign of the base assembly and not complete redesign of the actuation modules.

This invention has been described in terms of specific embodiments set forth in detail, but it should be understood that these are by way of illustration only and that the invention is not necessarily limited thereto. Modifications and variations will be apparent from the disclosure and may be resorted to without departing from the spirit of the invention, as those skilled in the art will readily understand. Accordingly, such variations and modifications of the disclosed products are considered to be within the purview and scope of the invention and the following claims.

What is claimed is:

1. In transfer apparatus for transferring a liquid between chambers of a chemical reaction pack and comprising a first station for supporting a chemical reaction pack, the station comprising at least one supporting surface and pressure application means opposite to said surface for applying external pressure against at least one chamber of the reaction pack to transfer liquid between the chambers;

the improvement wherein at least one additional station is disposed adjacent to said one station, said stations being provided by three spaced apart modules arranged side-by-side, at least the middle one of the three having as one of its major surfaces, the supporting surface supporting a chemical reaction pack, and as another major surface opposite to said one major surface, a surface in which the pressure application means is disposed, so that the pressure application means of one module acts upon a chemical reaction pack supported by the opposite supporting surface of an adjacent module, therefore allowing for the simultaneous processing of a plurality of reaction packs.

2. The apparatus according to claim 1 wherein each module means defines two generally planar major surfaces which extend substantially parallel relative to each other.

3. The apparatus according to claim 1 wherein said pressure application means includes piston means arranged for movement along a path extending generally orthogonal to a first major surface of said module under the influence of a pressurized fluid.

4. The apparatus according to claim 3 wherein said pressure applying means comprises a flexible membrane arranged for distention relative to an opposing major surface on a first module under the influence of a pressurized fluid.

5. The apparatus according to claim 1 wherein at least one of said modules further includes temperature-controlling means for heating and cooling the liquid within said reaction pack.

6. The apparatus according to claim 5 wherein said temperature control means comprises a first heater/cooler mechanism movably arranged in combination with a first module and a second heater/cooler mechanism carried by a second module in opposing relation with said first heater/cooler mechanism.

7. The apparatus according to claim 1, further including base assembly means for supporting said modules.

8. An apparatus for transferring a test liquid between chambers of a chemical reaction pack comprising first and second modules arranged relative to each other to define a chemical reaction pack receiving station therebetween, said first module including means distendable toward an opposing surface on said second module wherein said means are capable of applying external pressure against at least one chamber of said reaction pack.

9. The apparatus according to claim 8 wherein said second module includes temperature controlling means disposed on at least a portion of the surface of said module that faces an opposing surface on said first module for heating and cooling the liquid within said reaction pack.

10. The apparatus according to claim 8 wherein said distendable means comprises fluid operated piston means movable along a path extending toward said opposing surface on said second module.

11. The apparatus according to claim 8 further including means for supporting said first and second modules in an adjacent relationship relative to each other.

12. An apparatus for controlling the temperature of and for transferring a test liquid through a chemical reaction pack comprising:

a plurality of modules disposed in an adjacent relationship to each other to define chemical reaction pack receiving stations therebetween, said modules being spaced apart a distance approximating the thickness of a chemical reaction pack, with each module having first and second major surfaces which extend parallel to each other and parallel to like surfaces on an adjacent module, and wherein each module comprises temperature controlling means on at least a portion of said first major surface thereof for heating and cooling the test liquid in said reaction pack and operative means on at least a portion of said second major surface thereof for applying external pressure against a chemical reaction pack accommodated within a receiving station.

13. The apparatus according to claim 12 wherein said operative means includes a plurality of fluid operated pistons spaced apart along said second major surface of each of said modules.

14. The apparatus according to claim 13 wherein each module further includes means for supplying a fluid under pressure to said plurality of fluid operated pistons.

15. The apparatus according to claim 14 wherein said fluid is air.

16. The apparatus according to claim 13 wherein said plurality of fluid operated pistons comprises a rigid element.

17. The apparatus according to claim 13 wherein said plurality of fluid operated pistons comprises a flexible membrane.

18. The apparatus according to claim 13 wherein at least one of said plurality of fluid operated pistons has temperature controlling means and is capable of cooperating with an opposing piston located in an adjacent module to allow for both sides of chemical reaction pack to be temperature controlled.

19. The apparatus according to claim 12 further including means for supporting said modules in an adjacent spaced relationship relative to each other.

20. The apparatus according to claim 12 wherein each module is removably mounted on a support means, said support means providing energy sources to said temperature controlling means and said operative means.

* * * * *